ns Patent [19]

United States Patent [19]  
Vit

[11] 4,060,600
[45] Nov. 29, 1977

[54] TREATING TEETH
[75] Inventor: Jaroslav Vit, Belle Mead, N.J.
[73] Assignee: National Patent Development Corporation, New York, N.Y.
[21] Appl. No.: 301,073
[22] Filed: Oct. 26, 1972
[51] Int. Cl.$^2$ .......................... A61H 9/00; A61K 7/16
[52] U.S. Cl. .......................................... 424/53; 32/58; 128/66
[58] Field of Search .................................. 424/49–58; 32/58; 128/66

[56] References Cited
U.S. PATENT DOCUMENTS

| | | | |
|---|---|---|---|
| 1,435,498 | 11/1922 | Resnik | 424/53 |
| 3,590,121 | 6/1971 | Schiff et al. | 424/50 |
| 4,012,842 | 3/1977 | Vit | 32/58 |

FOREIGN PATENT DOCUMENTS

| | | | |
|---|---|---|---|
| 1,943,971 | 3/1971 | Germany | 424/54 |

OTHER PUBLICATIONS

Chemical Abstracts (1), vol. 73, entry 67908c, 1970.
Chemical Abstracts (2), vol. 76, entry 37290q, 1972 citing Stringer et al., J. Sanit. Eng. Div., Amer. Soc. Civil Eng. 1971, 97(SA6).
Morris, Rudolph's Research Conference, 4th. Rutgers, State U., New Brunswick, N. J. Proceedings, 1965, Principles and Applications of Water Chemistry, Pub. 1967, pp. 23–53.

Primary Examiner—Shep K. Rose
Attorney, Agent, or Firm—Cushman, Darby & Cushman

[57] ABSTRACT

A method of treating teeth in dentistry, for the prevention of calculus, removal of caries, and dissolving of plaque, comprises bringing into contact with the teeth an aqueous solution containing a hypochlorite of an alkali and/or alkaline earth metal, and an amino compound capable of forming water-soluble non-mucous irritating N-chloro and/or N-dichloro derivatives thereof. The amine may be tertiary, or rearranged to result in a secondary or primary amine. Preferably an excess of amine to hypochlorite is used, to faciliate demineralization of old plaque and caries. For maintenance of the desired pH, a buffering system may be included. The solution may be used as a mouth wash, or in the form of a jet stream or a pulsated jet stream through an applicator such as a hypodermic needle, or with a carrier in the form of a paste for application with a brush.

10 Claims, No Drawings

TREATING TEETH

This invention relates to the treatment of living teeth in dentistry.

An object of the invention is to provide a method of treating teeth in dentistry for the removal of plaque and caries, and prevention of the building up of calculus.

Another object is to provide a method of treating teeth in dentistry which removes only plaque and caries, whilst leaving the remainder of the tooth unaffected.

Yet another object is to provide a method of treating teeth in dentistry by dissolving away or dispersing plaque and caries, thus eliminating mechanical removal by drills, burrs and hand tools.

A still further object is to provide a method of treating teeth in dentistry which, even if accidentally prolonged beyond an optimum period, will remove only plaque and caries and leave the remainder of the tooth, e.g. dentine or enamel, entirely unaffected.

A still further object is to provide a method of treating teeth in dentistry, for removal of plaque and caries, which is completely painless to the patient, in that it avoids vibration resulting from use of power operated tools, and pressure on sensitive portions of a tooth by hand-manipulated tools.

According to the present invention, a method of treating teeth in dentistry, for the prevention of calculus, and/or the removal of caries, and/or the dissolving of plaque, comprises bringing into contact with the teeth an aqueous solution resulting upon mixing of a solution of (i) a hypochlorite selected from the group consisting of hypochlorites of alkali metals such as Li, Na, K, Rb, and Cs, and/or alkaline earth metals such as Ca, Sr, and Ba, and a solution of (ii) an amino compound capable of forming water-soluble non-mucous irritating N-chloro and/or N-dichloro derivatives.

The amino coumpound may be a tertiary amine which is placed in solution in that state to react directly with the hypochlorite, or there may be an initial rearrangement of a tertiary amine to give secondary and/or primary amines themselves capable of subsequently forming the desired N-chloro and N-dichloro derivatives.

It is preferred to utilise an excess of tertiary amine to hypochlorite, because many tertiary amines have chelating properties which help in demineralizing plaque and caries, prior to their dissolution. Accordingly, the method of the invention is applicable not only to fresh plaque and caries, but also to older plaque and caries which has become mineralized.

By way of example, a suitable tertiary amine is ethylene-diamine-tetra-acetic acid (EDTA), of which the formula is: $(HOOCCH_2)_2NCH_2CH_2IV(CH_2COOH)_2$.

In accordance with the method of this invention, the pH of the solution should be maintained between 8 and 12, and preferably 10.5 to 11.5 inclusive. In order to maintain the preferred pH range it is desirable, because hydrogen ions are generated during the decomposition of the N-chloro or N-dichloro compounds in aqueous solution, to add a buffer system to the solutions of dental treatment. Such buffer should be compatible with the N-chloro and N-dichloro compounds, that is, it should not have any deleterious effect on the same, and it should be non-toxic. Porates and phosphates are proposed as compatible salts for the formation of buffer systems, e.g.:

$Na_2HPO_4$
$Na_2B_4O_7$

Examples of amino compounds suitable for use in carrying out the method of this invention are:

Glycine: $NH_2CH_2COOH$
Sarcosine: $CH_3NHCH_2COOH$
Taurine: $NH_2CH_2CH_2SO_3H$
Sulfamic acid: $NH_2SO_3H$
2-aminoethanol: $NH_2CH_2CH_2OH$
Urea: $NH_2CONH_2$ The method of the present invention needs the solution only to be brought adequately into contact with the teeth for a short period to enable the plaque and caries to be dissolved, e.g. as a simple rinse in the mouth.

The removal may be accelerated by feeding the solution onto the affected tooth as a stream, and an erosive effect may be obtained as the plaque and carious material commences to dissolve. The erosive effect may itself be hastened by providing a pulsating stream which weakens the deposits of plaque and caries by alternate application of force followed by relaxation, resulting in mechanical fatiguing of the deposits.

By addition of a suitable carrier, e.g. a thickening agent, such as $SiO_2$, to form a paste, the solution may be more readily applied with an applicator such as a toothbrush or the like.

In carrying out the method the present invention, the following solutions have been found effective:

Solutions used
(Data are given in moles per liter of the water solution.)

|   | NaClO | NaOH | NaCl | Amino Compound | | Buffer Salt | | pH* |
|---|-------|------|------|------|------|------|------|------|
| A | 0.008 | 0.0539 | 0.050 | 0.05 | glycine | $Na_2HPO_4$ | 0.0025 | 11.59 |
| B | 0.008 | 0.0640 | 0.050 | 0.05 | glycine | $Na_2B_4O_7$ | 0.00125 | 10.77 |
| C | 0.008 | 0.0210 | 0.050 | 0.05 | glycine | $Na_2B_4O_7$ | 0.00125 | 9.65 |
| D | 0.008 | 0.0537 | 0.050 | 0.05 | sulfamic acid | $Na_2HPO_4$ | 0.0025 | 11.49 |
| E | 0.008 | 0.0520 | 0.052 | 0.05 | sulfamic acid | $Na_2B_4O_7$ | 0.00125 | 10.75 |
| F | 0.008 | 0.0548 | 0.050 | 0.05 | taurine | $Na_2HPO_4$ | 0.0025 | 11.86 |

*The pH value of all solutions tested remained constant within 0.2 pH units for at least one hour.

The following is a first example of preparation of a decayed tooth for filling:

The solutions of the previous paragraph were applied as a liquid stream at a temperature of 35°–45° C, and preferably a body temperature circa 37° C, on a carious area of a decayed tooth. The solution was applied either at a steady pressure in the range of 10 to 100 psi., or as a pulsating jet stream where the pressure is varied from 0 to 10 psi. or from 0 to 40 psi., or from 0 to 80 psi., or from 0 to 100 psi., during one cycle at a frequency of 100 to 1500 cycles per minute through a hypodermic needle of 20 to 23 gauge. However the pressure in either case can be increased to 200 psi.

Each tooth was substantially clean and ready to fill within 1 to 7 minutes, depending on the size of the cavity and its location. Judged by qualitative eye observation, the removal of caries is more effective on living unextracted teeth than on extracted teeth. A pulsating jet stream was found to be more efficient than a non-pulsating stream, even though more of the cleansing solution was used in the non-pulsating jet stream.

The following is a table showing the results obtained, using the solutions "A" to "F" of the list given earlier in this specification:

| Solution | Temp. (°C) | Needle Gauge | Caries Removal Frequency (c/min) | Pressure (psi) | Volume (ml) | Time for Complete Removal (min) |
|---|---|---|---|---|---|---|
| A | 37 | 20 | 850 | 0–10 | 430 | 3.5 |
| A | 37 | 20 | 650 | 0–40 | 380 | 4.5 |
| A | 36 | 20 | 700 | 0–40 | 500 | 4.5 |
| A | 37 | 20 | 200 | 0–100 | 470 | 6.0 |
| A | 37 | 23 | —* | 40* | 1150 | 11 |
| B | 38 | 20 | 100 | 0–80 | 480 | 4.5 |
| C | 37 | 20 | 1100 | 0–40 | 460 | 5.0 |
| D | 39 | 20 | 750 | 0–40 | 420 | 5.5 |
| A | 38 | 23 | 1500 | 0–100 | 510 | 7.0 |
| A | 45 | 20 | 550 | 0–40 | 570 | 3.5 |
| A | 35 | 20 | 800 | 0–80 | 490 | 1.0 |
| E | 37 | 20 | 650 | 0–40 | 480 | 4.5 |
| F | 38 | 20 | 800 | 0–80 | 590 | 6.0 |

*Constant non-pulsating jet stream.

All teeth were filled with a temporary filling and the patients' blood and urine samples were tested both before and after treatment. After 30 days, the temporary fillings were removed and the teeth examined. All of them were found to be ready to receive permanent fillings. In some cases, depending on the configuration of the cavity, a small degree of undercutting using a regular dental drill was necessary, but solely in order to provide a suitable internal configuration of the cavity to anchor the permanent filling. Blood and urine samples were again taken. These samples gave results essentially identical to those previously obtained. No apparent side effects, either systemic or local, where found. The treatment was reported by the patients to be completely painless. Only the decayed material was removed, and no effect was observed on any healthy tooth tissue or mucous membranes.

A major advantage of this method of treatment, as compared to the established drilling procedure, is that even if the treatment is greatly prolonged (i.e., continued long after all the carious material is removed), no removal of or damage to healthy tooth tissue — dentine or enamel — results. This is, however, not the case if mechanical drilling is accidently prolonged.

The stability of the solutions of the present invention is limited, and it is preferred to use solutions which have been recently freshly prepared.

The following is a second example of preparation of a decayed tooth for filling:

An active solution was generated by mixing equal amounts of a 0.5% sodium hypochlorite solution with a 0.5 Molar solution of EDTA. The pH of the EDTA solution was adjusted to 10.5 before mixing. The final solution was used at a temperature of 36° C. This solution was applied in the form of a pulsating jet stream of which the pressure varied from 0–80 psi. during one cycle at a frequency of 700 cycles per minute through a 20 gauge needle. The tooth was essentially clean and ready to fill within 5 minutes.

The following is an example of carrying out the method of this invention utilising the solution as a mouth wash:

An active solution was prepared by mixing equal amounts of 0.2% sodium hypochlorite solution and 0.3 Molar EDTA solution at room temperature. A 20 ml. portion was taken and used for rinsing the patient's oral cavity. The solution was used for approximately one minute. The above procedure was repeated one time for a total rinsing time of 2 minutes.

We claim:

1. A method of treating teeth in dentistry, for the purpose of prevention of calculus, removal of caries or dissolving plaque which comprises bringing into contact with the teeth an amount of an aqueous solution effective for such purpose containing the reaction product resulting from mixing a solution of (1) a hypochlorite selected from the group consisting of the hypochlorites of Li, Na, K, Rb, Cs, Ca, Sr and Ba and a solution of (2) ethylene diamine tetra acetic acid.

2. The method claimed in claim 1, wherein the solution is applied to the oral cavity as a mouth wash.

3. The method claimed in claim 1, wherein the solution is applied to a tooth as a jet stream.

4. The method claimed in claim 1 wherein the solution is applied to a tooth as a pulsated jet stream.

5. The method claimed in claim 1 wherein the solution is in a paste and is applied to the teeth with a brush.

6. A method according to claim 1 wherein the hypochlorite is sodium hypochlorite.

7. A method according to claim 1 wherein the composition has a pH in the range of 8 to 12.

8. A method according to claim 7 wherein the solution comprises a non-toxic buffer to maintain the pH within said range.

9. A method according to claim 8 wherein the pH is 10.5 to 11.5.

10. A method according to claim 9 wherein the composition is made from equal amounts of a 0.5% solution of sodium hypochlorite and a 0.5% molar solution of ethylene diamine tetra acetic acid.

* * * * *